United States Patent [19]
Atherton

[11] Patent Number: 6,127,823
[45] Date of Patent: Oct. 3, 2000

[54] ELECTROMAGNETIC METHOD FOR NON-DESTRUCTIVE TESTING OF PRESTRESSED CONCRETE PIPES FOR BROKEN PRESTRESSING WIRES

[76] Inventor: David L. Atherton, 2021 Morrison Road. R.R.#2 Perth Road., Ontario, Canada, K0H 2L0

[21] Appl. No.: 08/946,989

[22] Filed: Oct. 8, 1997

[51] Int. Cl.[7] .................................................. G01N 27/82
[52] U.S. Cl. .......................................... 324/220; 324/240
[58] Field of Search ..................................... 324/219, 220, 324/221, 228, 230–243; 340/673, 676

[56] References Cited

U.S. PATENT DOCUMENTS

| | | | |
|---|---|---|---|
| 3,651,506 | 3/1972 | Olaf et al. ............................... | 340/676 |
| 3,834,524 | 9/1974 | Ratz et al. ............................... | 340/676 |
| 4,806,863 | 2/1989 | White ....................................... | 324/238 |
| 4,814,702 | 3/1989 | Driggers et al. ........................ | 324/220 |
| 5,168,266 | 12/1992 | Fukuda .................................... | 340/676 |

*Primary Examiner*—Jay Patidar
*Attorney, Agent, or Firm*—Richard J. Hicks

[57] ABSTRACT

A method for detecting breaks in a prestressed wire, rod or bar embedded in concrete surrounding a metal pipe is described. A remote field eddy current probe is traversed axially internally through the pipe so as to create an energy flow path externally of the pipe and a transformer coupling through the pipe, and generate a signal in a detector coil axially spaced from an exciter coil. As the exciter coil traverses the wire, rod or bar containing the break a signal change is generated, regardless of the radial position of the detector coil relative to the break.

10 Claims, 9 Drawing Sheets

ELECTROMAGNETIC METHOD FOR NON-DESTRUCTIVE TESTING OF PRESTRESSED CONCRETE PIPES FOR BROKEN PRESTRESSING WIRES

FIELD OF INVENTION

This invention relates to methods for non-destructive testing of prestressed concrete pressure pipes. More particularly this invention relates to remote-field eddy current (RFEC) and/or transformer coupling (TC) methods for testing prestressed concrete pressure pipes.

BACKGROUND OF INVENTION

Non-destructive testing of large diameter steel pipes such as natural gas pipelines using magnetic-inspection techniques is well known in the art. Tools fitted with magnetic flux leakage (MFL) anomaly detectors embodying strong permanent magnets to magnetize the pipe wall to near saturation flux density are generally employed. Sensors, moving with the detectors, have signals induced by variations in the leakage fields caused by such pipe-wall anomalies as internal or external corrosion, hard spots and so on, and including local variations in the magnetic permeability. MFL anomaly detectors are, however, subject to problems caused by such things as noise, hostile operating environment, restricted power due to battery capacity and finite data storage capacity. Thick walled or small diameter pipes are more difficult to inspect by the MFL anomaly technique because there is frequently little space available inside such pipes for magnets compared to the relatively large pipe-wall cross sectional area to be driven into magnetic saturation. While this problem has been alleviated in recent years following the introduction of neodymium-iron-boron (NdFeB) permanent magnets which have improved mechanical and magnetic properties and can produce higher usable flux densities than the earlier ferrite magnets and are mechanically stronger than cobalt-rare earth magnets, MFL anomaly techniques are generally limited to essentially direct contact inspection and are not generally suitable for indirect coupling through air or other materials or when there is appreciable sensor liftoff. Remote field eddy-current (RFEC) devices have been developed for these latter tasks. RFEC devices incorporate, transmit and receive coils, and use a solenoidal exciter coil, energized with low frequency ac (typically, 20–2000 Hertz), internal to and generally approximately coaxial with the longitudinal axis of the pipe to be tested. It has been found that the operating frequencies for non-ferromagnetic tubes, such as reactor pressure tubes, are much higher at about 10 kHz, than those suitable for ferromagnetic pipes which are typically about 60 Hz. Low frequencies imply low scanning speeds. The detector coil, or array of detector coils, is placed adjacent the inside of the pipe wall and axially or radially aligned. The exciter coil or coils are displaced longitudinally along the pipe from the exciter coil by about 2 to 3 pipe diameters (D). At this separation direct coupling between the exciter and the detector is strongly attenuated by the pipe. The signal in the detector results principally from an indirect energy transmission path on the outside of the pipe. Field from the exciter diffuses through the pipe wall in the vicinity of the exciter, being attenuated and phase shifted in the process. Once on the outside, this energy then radiates with relatively little attenuation. In the case of a ferromagnetic pipe, it tends to be guided preferentially in the axial direction.

Adjacent the remote detector coil, the field on the outside of the pipe is much greater than the field inside, which is generated largely by energy which diffuses back from the outside, again being attenuated and further phase shifted in the process. Anomalies anywhere in this energy-transmission path will cause changes in the phase and amplitude of the received signal. Because the received signals are small, typically of the order of 10 $\mu$v, a phase sensitive synchronous detector or lock-in amplifier is incorporated to receive and amplify the signal.

While RFEC probes have now been used for many years for well-casing inspection and more recently for heat exchangers and pressure tubes, the phenomenon is complex and defect responses are still not fully understood.

Large diameter concrete lined steel pipes or cylinders have been used to convey water for many years and such pipes are frequently provided with a spirally wound high strength prestressing wire which is pre-tensioned before a top coating of mortar is applied. In some instances a layer of concrete is also applied to the outside of the steel pipe before the prestressing rod, bar or wire is applied and a second layer of mortar is applied on top of the rod, bar or wire spiral. While rupture of prestressed concrete pipe is relatively uncommon, nevertheless periodic inspection of municipal water supply pipes and the like, which have an expected service life of 30 years or more, would be advantageous in order to prevent expensive ruptures or other failures. Heretofore, however, there has not been any practical method for inspecting composite pipes, such as prestressed concrete pipes.

OBJECT OF INVENTION

An object of the present invention is, therefore, to provide a method for inspecting the steel prestressing wire or rods included in high pressure concrete pressure pipes (CPP) embedded in concrete in situ.

BRIEF STATEMENT OF INVENTION

By one aspect of this invention there is provided a method for detecting discontinuities in a prestressing wire or rods embedded in concrete surrounding a metal pipe comprising:

passing a remote field eddy current probe, comprising a coaxially-wound exciter coil and a detector coil axially spaced therefrom, axially through said prestressed pipe;

energizing said exciter coil with low frequency ac, so as to create an energy flow path externally of said pipe between said exciter coil and said detector coil and a transformer coupling through said prestressing wire or rods inductively linking said exciter coil and said detector coil; and receiving a signal in said detector coil indicative of discontinuities in said prestressing wire. dr

DETAILED DESCRIPTION OF PREFERRED EMBODIMENTS

Figure 1:
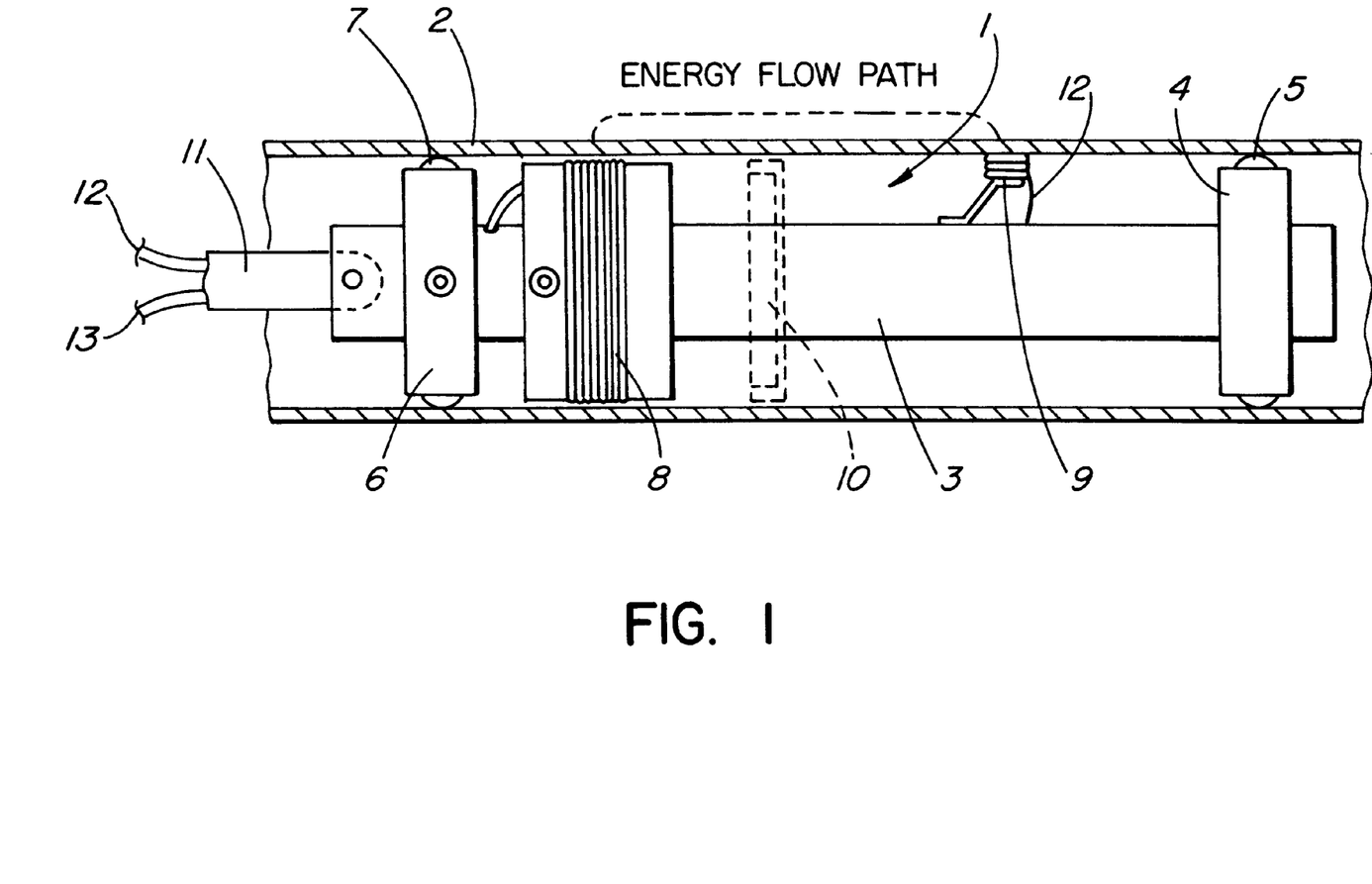
FIG. 1 is a cross sectional view of a simplified remote field probe contained within a cylindrical pipe.

An example of a simplified remote field probe 1 in a pipe 2 is shown in FIG. 1, and comprises a cylindrical body 3 having a forward carriage 4 having wheels 5 for rolling engagement with pipe 2 and a rearward carriage 6 having wheels 7 for rolling engagement with pipe 2, mounted at respective ends thereof. Other mounting means such as skids, brushes, cups or discs may also be employed. Intermediate carriages 4 and 6 there is provided a solenoidal exciter coil 8 approximately coaxial with cylindrical body 3 and a detector coil 9 or circumferential or axial array of detector coils 9 axially displaced from coil 8 by about two pipe diameters (see FIG. 4b). Optionally one or more radially extending radiation shields 10 are provided between coils 8 and 9. A drive rod, cable or wire 11 is provided adjacent carriage 6, which rod may be a hollow rod to carry signal cables 12 and a power cable 13. A commercially available device of this type, under the tradename "HYDROSCOPE" can be obtained from Hydroscope Inc. of Edmonton, Alberta, Canada.

Figure 4A:
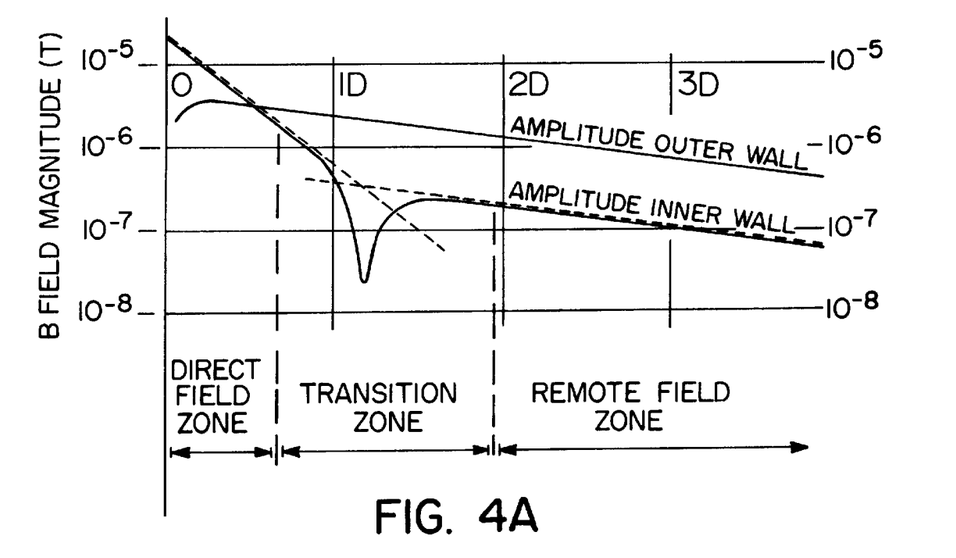
FIG. 4A is a graph illustrating the B field magnitude profile inside and outside a pipe.

As described herein above when exciter coil 8 is energized with low frequency ac (20–200 Hz), a magnetic field is generated and diffuses through the pipe wall in the vicinity of the exciter being attenuated and phase shifted in accordance with eddy current principles. Once on the outside this energy radiates with relatively little attenuation and, with a ferromagnetic pipe, tends to be guided preferentially in the axial direction along the outer wall since low frequency magnetic fields impinge nearly radially on the wall to give a predominantly axial Poynting vector. In the remote-field region, the field on the outside of the pipe is much greater than the field inside (as shown in FIG. 4A), which is generated largely by energy which diffuses back from the outside, again being attenuated by the circumferential eddy currents induced in the pipe's wall and further phase shifted in the process. Anomalies anywhere in this external energy transmission path will cause changes in the phase and amplitude of the signal received at the detector coil 9. The received signal is carried by cable 12 to a phase-sensitive detector or lock-in amplifier (not shown).

Figure 2:
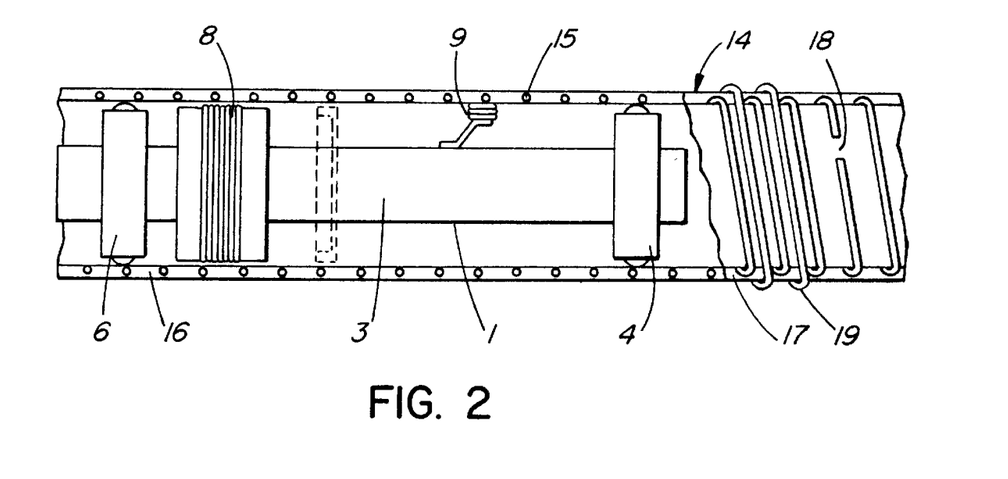
FIG. 2 is a side view of a wire-wound prestressed concrete pipe, partially in cross section.
Figure 3:
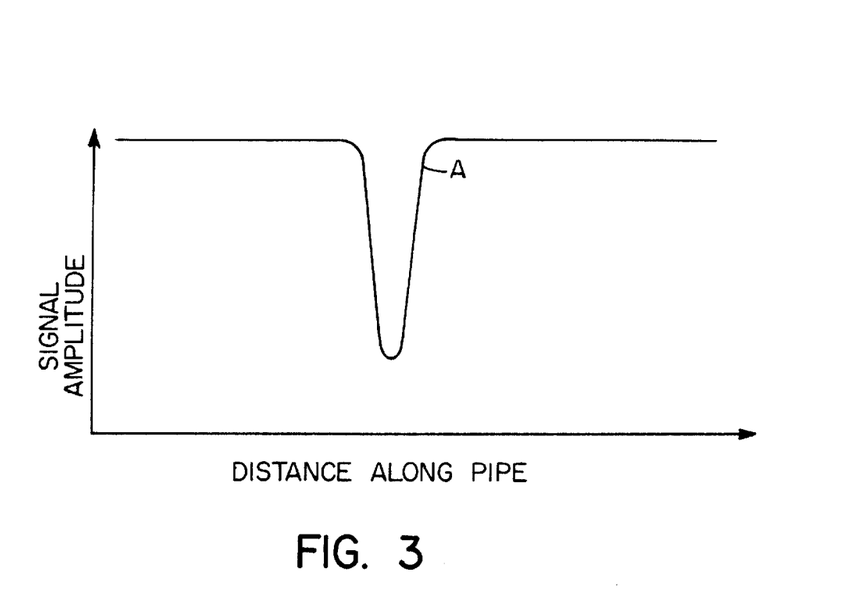
FIG. 3 is a graph illustrating the amplitude of received signal relative to position of the probe of FIG. 1 in the pipe.

FIG. 2 shows the probe 1 in a wire wound prestressed concrete pressure pipe 16. A concrete core is cast on the inner wall of a thin steel cylinder. An outer concrete core may also be cast onto the outer wall of the steel cylinder. A high strength steel prestressing wire 15 is then spirally wound on under high tension and a protective mortar coating 14 applied. If desired, one or more additional prestressing wires 19 may be added, as shown in FIG. 2. Wire 15 is a generally continuous spiral but if later corrosion causes even a single break 18 in one turn thereof, as probe 1 is advanced in the direction of the arrow an amplified read out signal from the detector may be observed, as shown in the graph of FIG. 3, in relation to the position of probe 1 in pipe 16. As the probe approaches the defect/break 18, the signal amplitude changes abruptly as detector coil 9 traverses the defect 18. It has been found that the change in signal A occurs when detector 9 is adjacent the specific turn of wire 15 containing defect 18. It is not necessary for coil 9 to be circumferentially adjacent defect 18 in order to generate the signal change. It will be appreciated, therefore, that a defect in the spirally wound wire can be detected by a pass of the probe 1 through pipe 14.

Figure 5A:
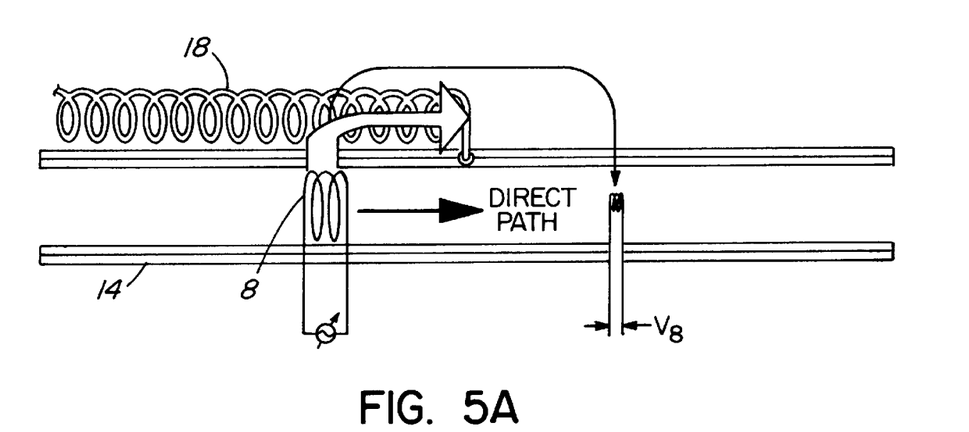
FIG. 5a is a schematic diagram illustrating transformer coupling in prestressed CPP, when the exciter is under a set of windings and the detector coil is outside the winding region.
Figure 5B:
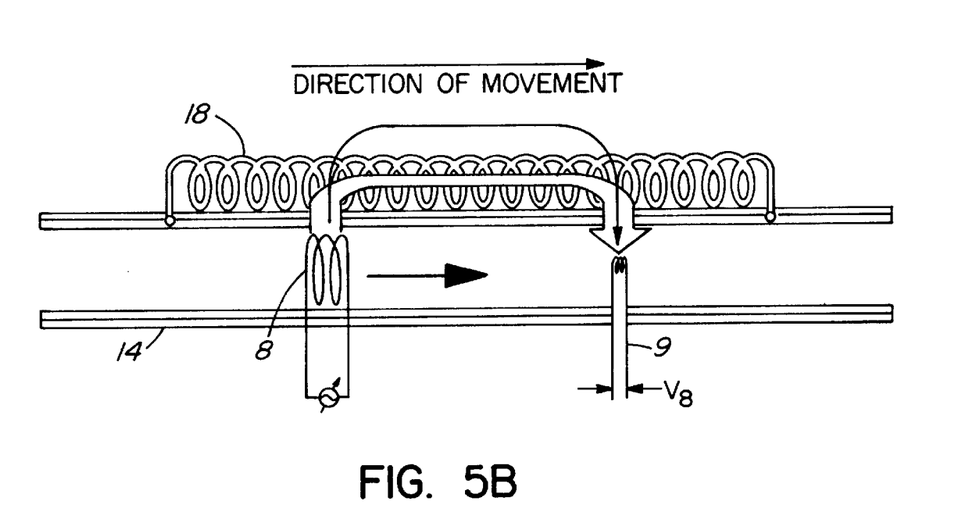
FIG. 5b is a schematic diagram, similar to FIG. 5a, except that the exciter and detector are under the same set of windings.
Figure 6:
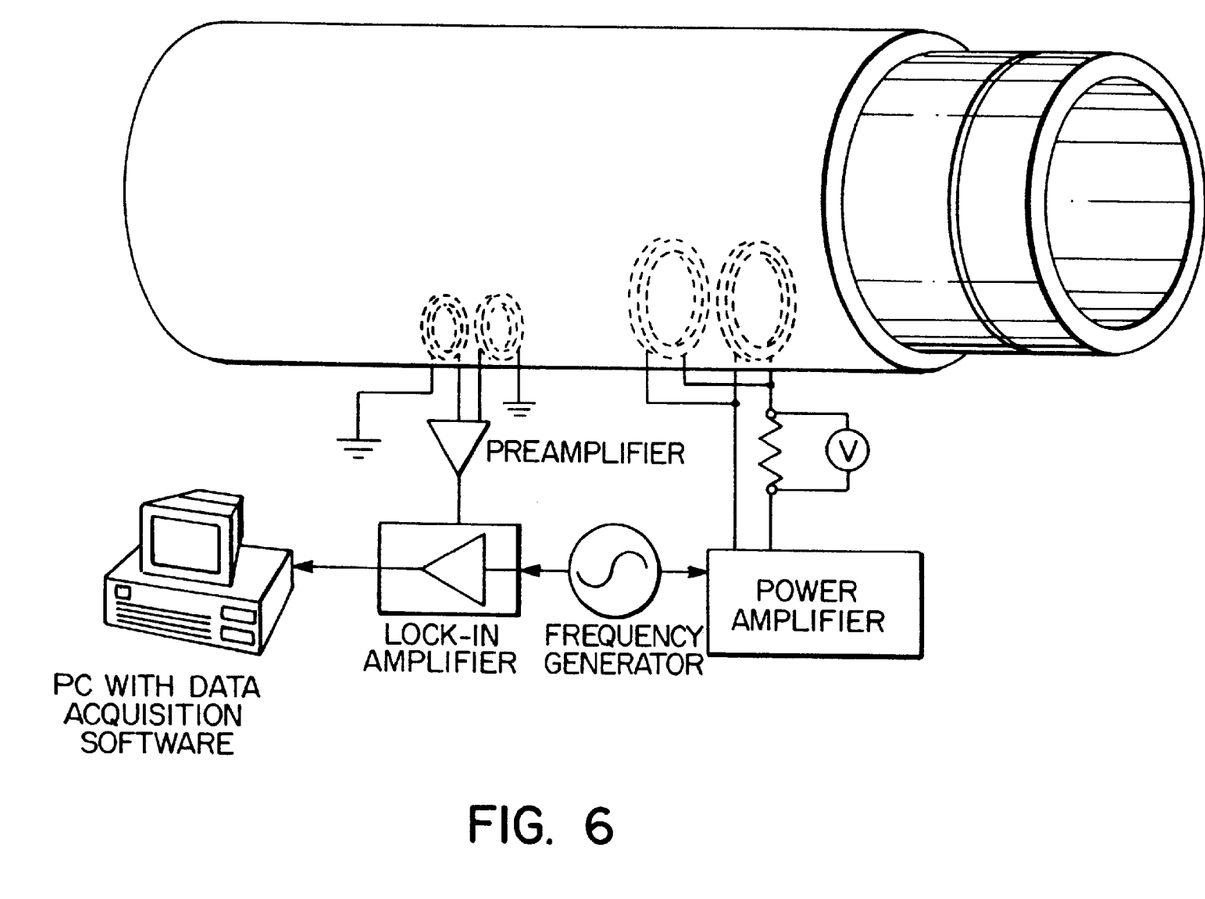
FIG. 6 is a schematic diagram of an experimental apparatus to detect breaks in CPP.

FIGS. 5a and 5b illustrate schematically a transformer coupling effect (TC). The relative position of the exciter 8, detector 9 and surface/prestressing windings 18 (shown for simplicity outside the cylinder rather than axially, determines the effectiveness of the TC. It will be appreciated that exciter 8 and detector 9 may both be either a single coil or may be a plurality of coils, as shown in FIG. 6. In FIG. 5a the exciter is under a set of surface windings while the detector coil is outside the winding region. The direct path is strongly attenuated, since the inter-coil distance is more than two pipe diameters. The TC through the surface windings is absent, so only the RFEC linkage remains. When the RFEC/TC probe exciter 8 and the detector 9 are both under the same set of surface windings 18, as shown in FIG. 5b, a strong transformer coupling then exists between the exciter 8 and detector 9 superimposed on the weaker direct and remote field paths. Provided the energy coupling path between the exciter and detector coils is predominantly outside of the steel cylinder, i.e. the coil separation is sufficient to satisfy the remote field condition, the external coupling can be greatly enhanced by the emdedded prestressing wire winding which is simulated by a surface winding. The prestressing wire, forms an enclosing winding magnetically coupling the exciter and detector coils, provided that they are both within the winding and that it is complete. The simplest model to use to describe the results is then to consider that, in addition to remote field effects, the prestressing winding should be considered as an additional strong transformer coupling coil which can link the detector and exciter inductively. Both effects are important so the method may be described as RFEC/TC.

Currents, which are easily measurable, are induced in an encircling external coupling coil such as formed by the prestressing wire when the exciter is within it. The winding then acts as a solenoidal coil. This generates fields which can be received by an axial detector any time that both the exciter and detector are within the closed prestressing winding. A radial field detector coil will have an induced signal only relatively close to the inside wall near the end of the winding, provided that the exciter is within it. If even a single turn of the winding is cut or corroded through these signals from the additional strong transformer coupling can be lost. It has been confirmed experimentally that the axial field is indeed detected with very large lift offs. These signals are, of course, in addition to RFEC signals from pipe joints, etc.

Figure 4B:
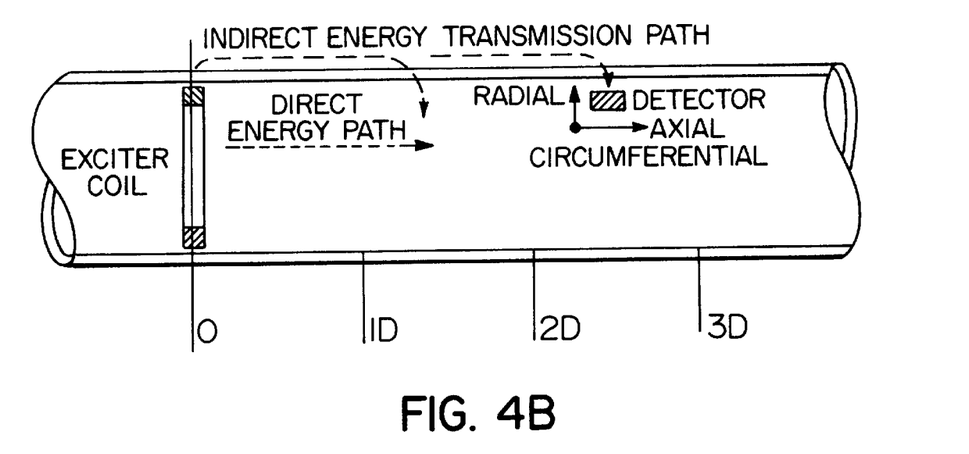
FIG. 4B is a schematic diagram of an RFEC probe in pipe showing direct and indirect energy flow paths.

Several important points about the use of RFEC/TC techniques for CPP prestressing wire monitoring should be noted:

1) To monitor the prestressing wire the coupling between the exciter and detector must be predominantly outside of the cylinder, i.e. it must follow the indirect RFEC energy transmission path indicated in FIG. 4. The detector must therefore be well into the remote field region, typically, but not necessarily, two or more pipe diameters from the exciter, under all conditions. This indirect energy transmission path can then be enhanced by the transformer coupling (TC) effect of the coil formed by the prestressing wire, as shown in FIG. 5.

2) Irregularities in the pipe wall (or steel cylinder), most notably pipe joints, cause changes in both the outward and inward diffusion paths as either the exciter or detector pass and therefore show two responses on the signal logs.

3) The RFEC/TC signal logs contain responses from irregularities in both the cylinder and the prestressing wire.

4) Conventional RFEC inspection probes use either a relatively large coaxial detector or a circumferential array of detectors to obtain full coverage of the pipe wall. RFEC/TC probes for prestressing wire in CPP may use only a single relatively small detector coil to obtain full circumferential coverage for discontinuities in the winding.

5) Conventional RFEC probes normally aim to have relatively large exciter coil/pipe fill factors. This is not necessary for CPP inspection—150 mm probes in both 400 mm and 600 mm pipes have been demonstrated. Although the RFEC/TC probes may be long, they can be simply jointed to access large diameter CPP through customary 500 mm man holes.

EXAMPLE 1

Preliminary small scale tests using galvanized ducting spiral wrapped with oiled black iron wire have been conducted. Cuts in the wire interrupted the regular periodic RFEC responses obtained when an RFEC probe with a single small detector coil near the inner wall of the duct was pulled through. These encouraging results led to extended tests on samples of 400 and 600 mm prestressed lined cylinder CPP.

Initial tests of the effects of a cut in the prestressing wire in the 600 mm CPP sample were encouraging as significant changes were obtained in the logs obtained pulling through an RFEC tool with a single small radial field detector coil. It was however noted that the background variability in the 400 mm CPP was relatively large and, in addition, that the background variability in the 600 mm CPP also increased markedly over a period of months. This is believed to be due to electrical conductance between the cylinder and the prestressing wire, which is wound onto the cylinder for the concrete lined CPP, changing both spatially and over time due to natural curing. Despite the strong signals obtained from prestressing wire breaks they may be masked by the variability of the background. Efforts have, therefore, been concentrated on embedded cylinder CPP (which has an additional layer of concrete between the cylinder and the prestressing wire).

Large diameter embedded cylinder CPP is massive and was, therefore, simulated by surface windings on the outside of the mortar coating on smaller 400 mm and 600 mm lined cylinder CPP. These tests were believed to be a reasonable simulation of embedded cylinder CPP since there is also a "direct winding" of prestressing wire wrapped directly onto the steel cylinder, in addition to the surface winding on the outside. The direct winding likely produces considerably greater background variation than found in real embedded cylinder CPP, again because of the varying conductances between the cylinder and prestressing wire. Anomalies in this direct winding on the test pipes are detectable with the RFEC/TC tool, but cannot be examined without removing the mortar layer. Both the direct and simulated prestressing windings have a similar helix pitch of 40 mm. The surface winding can easily be cut or connected to the ends of the pipe cylinder. The resulting changes in the amplitude or phase logs can then be noted.

FIG. 6 shows an experimental apparatus used to generate the sinusoidal exciter field and to detect, amplify and record the RFEC/TC signal. Operating frequencies of 140 Hz in the 600 mm pipe, and 190 Hz in the 400 mm pipe were used. A current of 0.280 A was delivered to a 150 mm diameter, 1000 turn exciter coil. Small diameter detector coils were used to measure both the axial and radial field components. The detector was positioned 1.2 m axially away from the exciter coil, corresponding to three pipe diameters in the 400 mm pipe. This ensured that the tool operated in the remote field region. For axial field measurements the detector coil lift off from the inside of the concrete core was typically 90 mm but axial signals are relatively insensitive to lift off and as much as 200 mm was used successfully. The lift off was reduced to 25 mm or less for radial field scans since, with increasing lift off, the radial amplitude decreases rapidly and the signal was soon lost in background noise.

The detector amplitude and phase were sampled at 20 Hz, giving adequate resolution to discern breaks in the prestressing wires, or the location of pipe joints. The RFEC/TC tool was pulled through the CPP with typical scan speeds of 20 m/min, but rates as high as 35 m/min were tested with little or no loss in resolution.

In the field, 6–7 m pipes are joined together to create a supply line. Each pipe has a male and a female joint spigot ring to permit a tight seal. Such a joint was simulated by cutting the 400 mm CPP and reversing the parts to join the male and female ends. An insulating layer was inserted in the joint. Two sets of surface windings were made, one on either side of the pipe junction. Each end of the surface windings was connected to the steel cylinder, creating two independent solenoidal windings. Both steel cylinders were also connected electrically at the joint.

Results and Discussion

With the presence of both direct and surface windings, the interpretation of RFEC/TC scans becomes complicated. It is helpful to compare the amplitude and phase logs of the small CPP with and without surface windings in order to develop an understanding of the responses. The axial and radial detector orientations also yield different information that can be considered. The varying conductances between the direct winding and the cylinder cause irregularities in the background signal so the figures presented here are processed scan logs from the 400 mm CPP. They have been processed to reduce the influence of the direct windings, and thus better simulate logs from embedded cylinder CPP.

Figure 7:
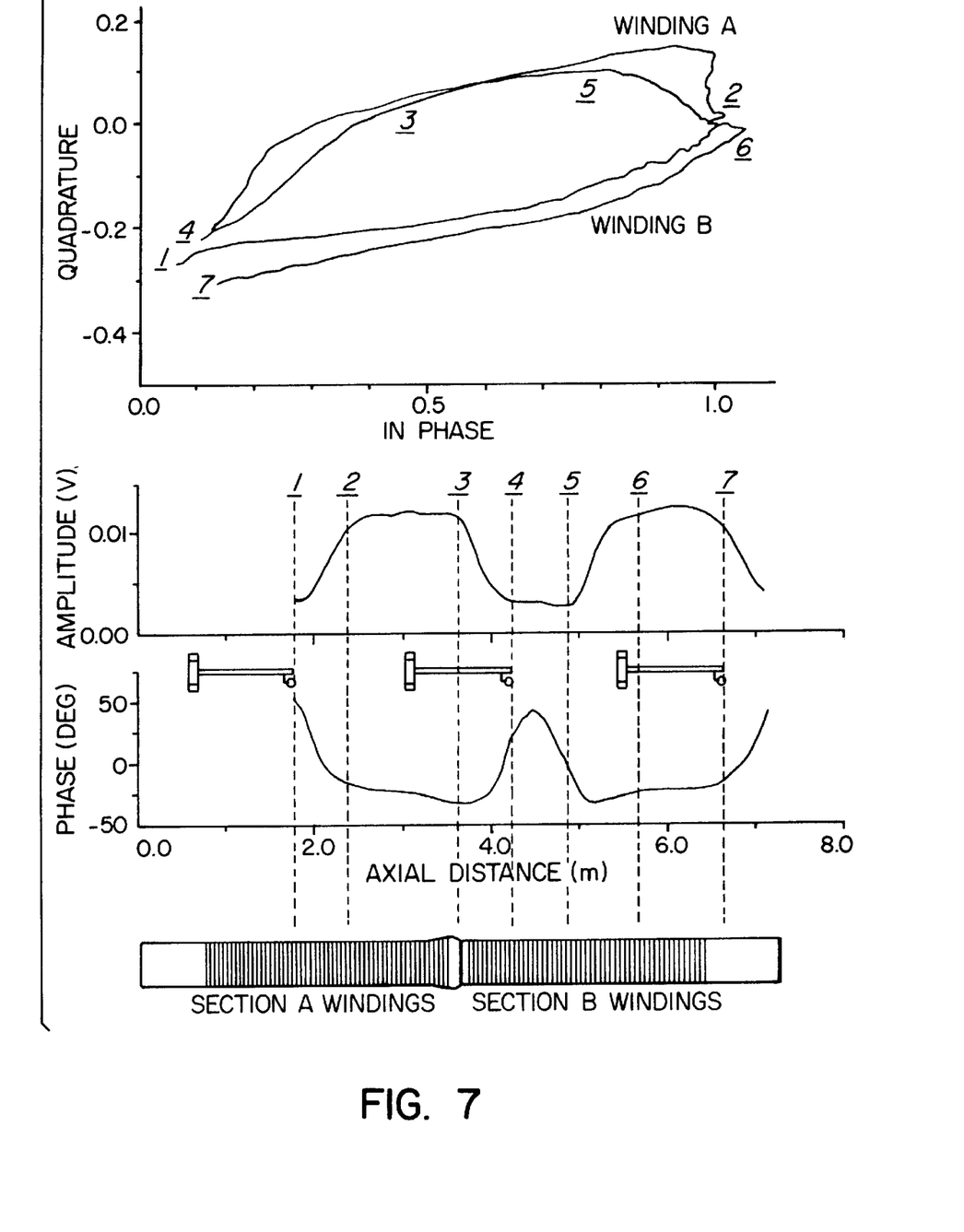
FIG. 7 is a simplified RFEC/TC axial amplitude (a) and phase logs (b) and a voltage plane polar plot (c) of the results of (a) and (b) in a laboratory simulation.

FIG. 7 shows, in the middle, axial amplitude and phase as functions of detector coil position in the pipe. A diagram of the 400 mm CPP showing the two surface windings and pipe joint, is shown at the bottom. A schematic of the RFEC/TC tool, to axial scale and with appropriate inter-coil distance, is superimposed on the amplitude and phase logs at several important positions. The voltage plane polar plot, shown at the top, is described subsequently. When both exciter and detector coils are under the same winding, the solenoid provides a strong TC path, as described in FIG. 5. This configuration occurs when the tool is between positions (2) and (3) and also between (6) and (7). The axial amplitude of the signal increases and the phase delay remains low, since this coupling between the exciter and detector is primarily inductive.

When the exciter is under the Section A windings, with the detector still beneath the Section B solenoid, the strong transformer coupling path is lost (see FIG. 3). This situation occurs when the axially-oriented detector coil is between (4) and (5). The amplitude is more strongly attenuated, and the signal takes more time to propagate, corresponding to an increase in phase lag. This type of analysis can be extended to explain the peaks and troughs on both the amplitude and phase logs.

The voltage plane polar plot representation of RFEC data is used to categorize and size defects in small diameter pipes and tubes. On the voltage plane polar plot, the RFEC signal amplitude is represented by the distance of a data point from the origin. Phase is represented by the angular rotation of the point the from x-axis, with increasing phase being counter-clockwise. The data is normalized generally with respect to a region of the pipe where the surface windings are undamaged and not grounded to the steel cylinder, referred to as the 'full wall signal'. The full wall signal is thereby set at the point (1,0) on the polar plot. The voltage plane polar plot representation allows both amplitude and phase to be analyzed simultaneously, and permits quick identification of both surface windings and pipe joints.

A simplified voltage plane polar plot is shown in the upper half of FIG. 7. When the exciter and detector are both under the same winding, as between (2) and (3) and also (6) and (7), the amplitude is high and the phase lag is low. Therefore, on this voltage plane representation, surface windings appear as large loops, labelled as Winding A and Winding B, running here from left to right. The joint between the two pipe segments, corresponding to region between (4) and (5) on the amplitude and phase logs, has increased phase lag and amplitude attenuation because of the effective increase in the thickness of the cylinder wall at the joint. The joint appears as a thin loop, here slanting downwardly to the left and labelled (4) on the voltage plane polar plot. By following the trace of the voltage plane from (1) through (7), the order of the features can be determined: one winding, then the joint, then the second independent winding.

Figure 8:
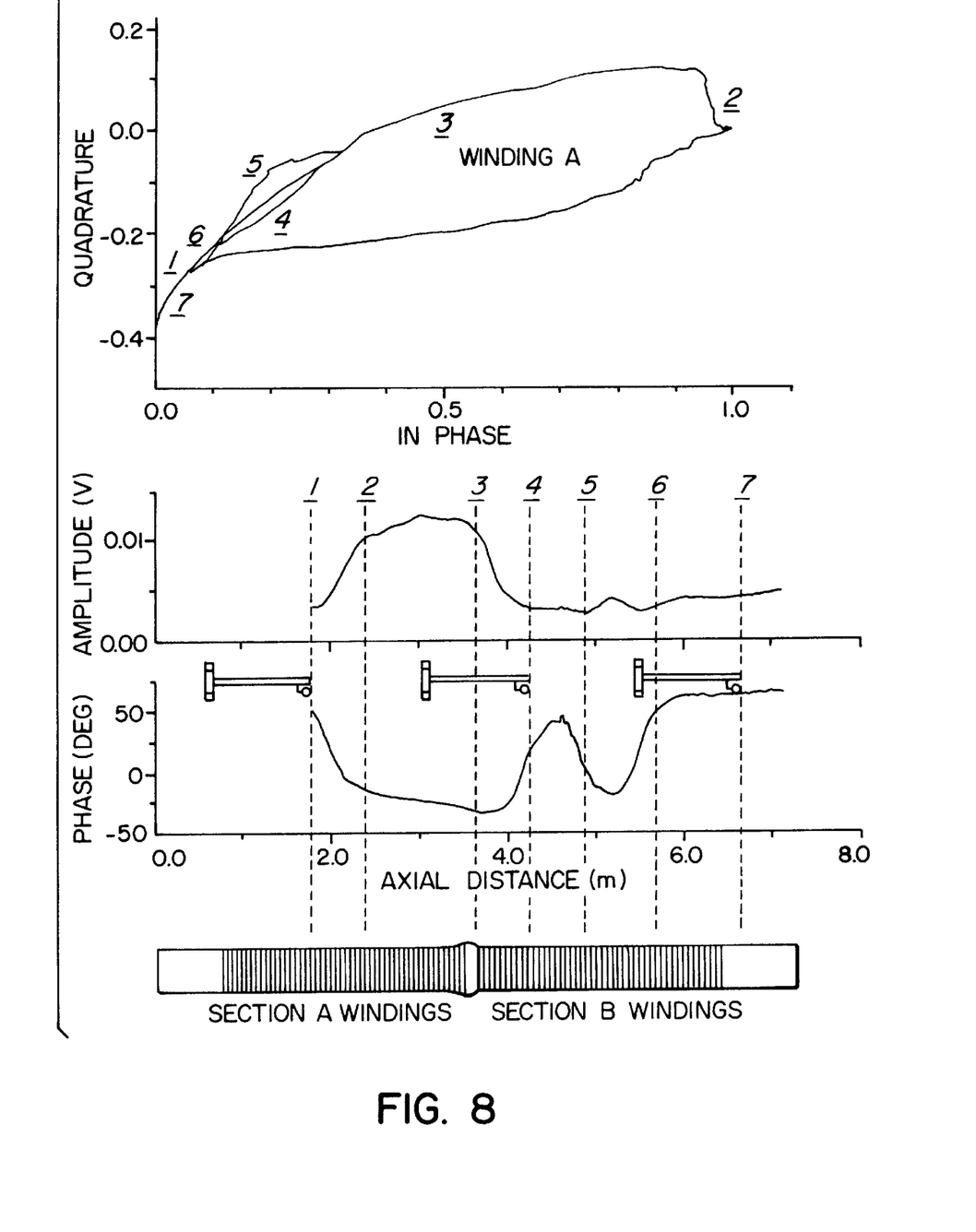
FIG. 8 is a simplified plot, similar to FIG. 7, in a laboratory simulation, except that winding B is cut.

FIG. 8 shows the same information as FIG. 7 but Winding B has been cut. The differences in the amplitude and phase logs are readily apparent but are even more obvious on the voltage plane polar plot where the large loop signature characterizing a surface winding is obviously missing for Winding B. Watching the responses being logged and the voltage plane polar plot being drawn in real time the missing anticipated signature for Winding B is even more dramatic.

The combination remote field/transformer coupling (RFEC/TC) technique described herein can detect even a single break or corrosion causing an open circuit in the prestressing wire used in embedded cylinder CPP (concrete on both sides of the steel pipe). The method exploits the through wall RFEC characteristics to monitor the prestressing wire in the indirect energy transmission path external to the steel cylinder within the CPP. There must therefore be sufficient axial distance between exciter and detector coils to ensure remote field operation. The indirect energy path external to the cylinder is greatly enhanced by the transformer coupling effect between the exciter and detector coils when the prestressing wire also forms a closed coil, with both exciter and detector coils within it. The prestressing wire winding then acts as a solenoid driven by the exciter coil. An open wire destroys this transformer coupling and is therefore readily detectable.

Although a radial field detector coil shows an induced signal near just one end of the prestressing winding—i.e. when it is also being driven by the exciter, an axial field detector coil shows an induced signal any time both the exciter and detector are within the closed prestressing winding. Very large detector lift offs are therefore possible and relatively small diameter (low fill factor) exciter coils can be used. RFEC/TC tools are therefore likely to be relatively long and thin.

Laboratory tests have generated good RFEC/TC logs at scanning speeds as high as 35 m/min. Voltage plane polar plots of the signal logs, developed for RFEC signal analysis, have shown that the signature traces from complete prestressing windings, broken windings and pipe joints can be readily distinguished.

Figure 9A:
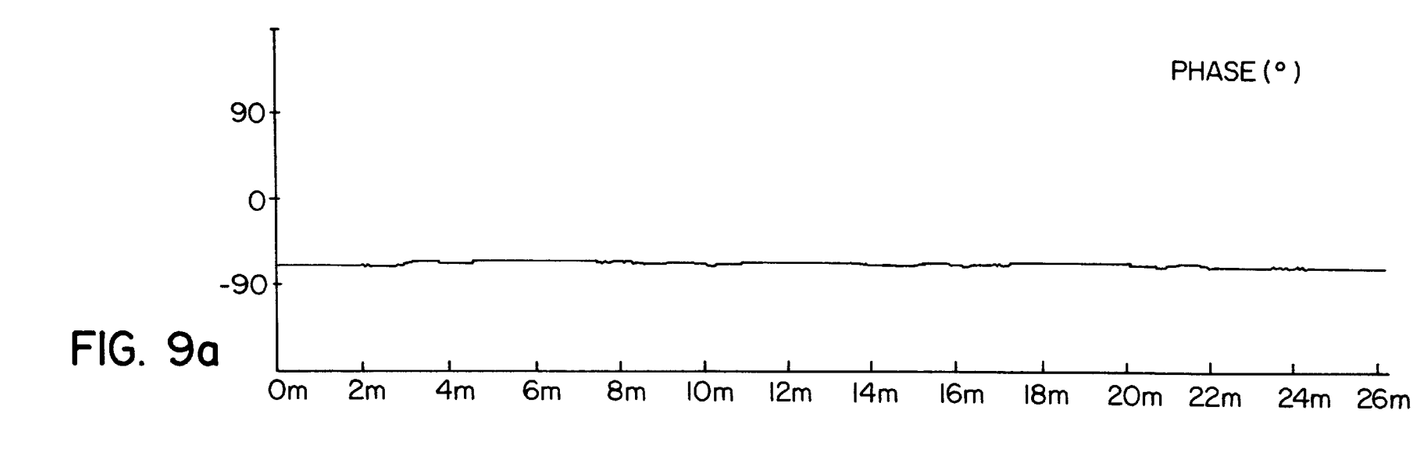
FIGS. 9a, and b are simplified plots, similar to FIGS. 7 and 8 in an actual full scale pipe.
Figure 9B:
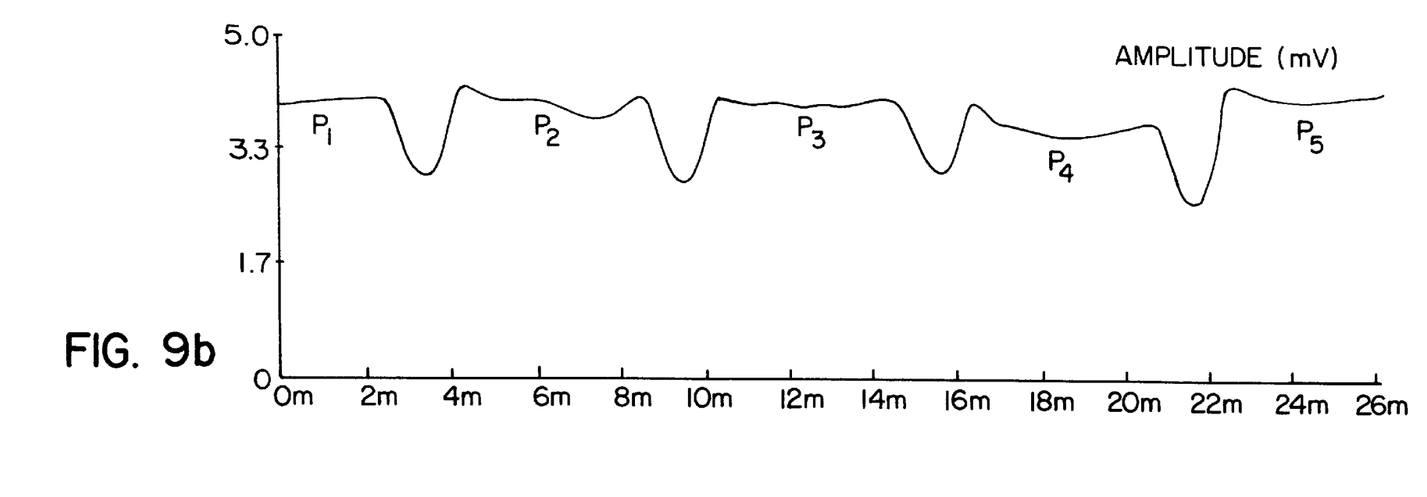
Figure 10:
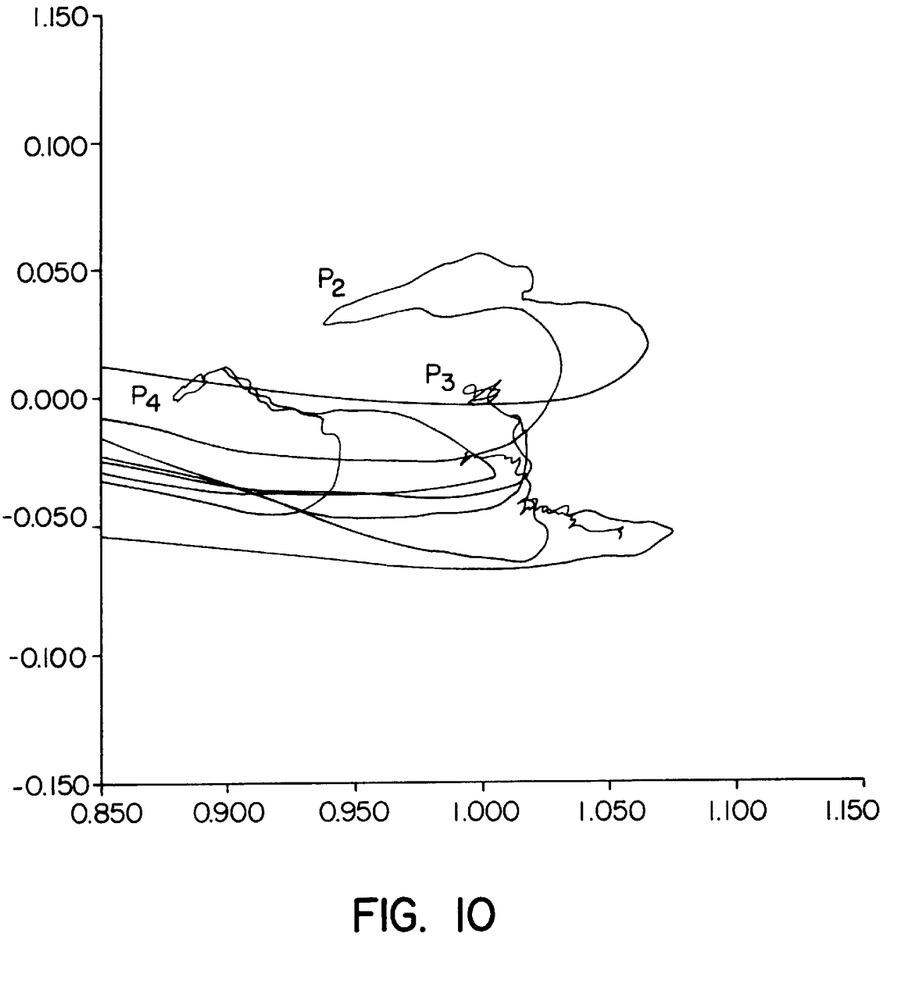
FIG. 10 is an expanded view of the polar plot of FIG. 9(b).

As noted above, interpretation of the test results is somewhat complicated but the amplitude (FIG. 9B) and phase shifts (FIG. 9A) of the received signals can be determined experimentally. From these data a voltage plane polar plot (FIG. 10) can be constructed according to the techniques described in "Remote Field Eddy Current Signal Analysis in Small-Bore Ferromagnetic Tubes", David D. Mackintosh et al, Materials Evaluation, April 1993, 492–500, the disclosure of which is incorporated herein by reference. Clearly from the polar plot of FIG. 10, it can be seen that individual defects or breaks can be readily identified. FIG. 10 illustrates a 48" CPP pipe with two cuts in the embedded wire in section 4, one cut in section 2 and one cut in section 3. It can be seen that the amplitude of the trace is dependent upon the number of cuts in the wire.

What is claimed is:

1. A method for detecting discontinuities in a spirally wound prestressing wire or rod embedded in concrete surrounding a metal pipe comprising:

passing a remote field eddy current probe, comprising a coaxially-wound exciter coil and a detector coil axially spaced therefrom, axially through said pipe;

energizing said exciter coil with low frequency ac, so as to create (a) an energy flow path externally of said metal pipe between said exciter coil and said detector coil and (b) a transformer coupling, through said prestressing wire or rod, inductively linking said exciter coil and said detector coil; and receiving a signal in said detector coil indicative of discontinuities in said prestressing wire or rod.

2. A method as claimed in claim 1 including the step of amplifying said signal from said detector coil.

3. A method as claimed in claim 1 wherein said prestressing wire or rod is electrically connected to said metal pipe.

4. A method as claimed in claim 1 wherein said signal comprises axial amplitude and phase logs.

5. A method as claimed in claim 4 including generating any form of voltage plane polar plot from said axial amplitude and phase logs.

6. A method as claimed in claim 1 wherein said prestressing wire or rod is a spiral, axially wound wire.

7. A method as claimed in claim 1 wherein said signal comprises radial amplitude and phase logs.

8. A method as claimed in claim 1 wherein at least one of said excitor and said detector comprises a plurality of coils.

9. A method as claimed in claim 1 wherein said prestressing wire or rod comprises a plurality of wires or rods.

10. A method as claimed in claim 1 wherein said signal comprises circumferential amplitude and phase logs.

* * * * *